(12) United States Patent
Stabel et al.

(10) Patent No.: US 8,361,280 B2
(45) Date of Patent: Jan. 29, 2013

(54) PROCESS FOR DISTILLATIVELY OBTAINING PURE 1,3-BUTADIENE FROM CRUDE 1,3-BUTADIENE

(75) Inventors: Uwe Stabel, Otterstadt (DE); Harry Zachmann, Ludwigshafen (DE); Eberhardt Gaffron, Lampertheim (DE); Bernd Heida, Ellerstadt (DE); Michael Jäger, Laudenbach (DE)

(73) Assignee: BASF SE, Ludwigshafen (DE)

( * ) Notice: Subject to any disclaimer, the term of this patent is extended or adjusted under 35 U.S.C. 154(b) by 577 days.

(21) Appl. No.: 12/611,465

(22) Filed: Nov. 3, 2009

(65) Prior Publication Data
US 2010/0126843 A1    May 27, 2010

(30) Foreign Application Priority Data
Nov. 24, 2008 (EP) ..................... 08169786

(51) Int. Cl.
C07C 7/04 (2006.01)
B01D 3/00 (2006.01)

(52) U.S. Cl. ............... 203/9; 203/49; 203/90; 585/809; 585/810; 202/269

(58) Field of Classification Search .............. 203/8–9, 203/49, 90; 585/809, 810; 277/12, 59
See application file for complete search history.

(56) References Cited

U.S. PATENT DOCUMENTS

| | | | | |
|---|---|---|---|---|
| 1,876,415 A | * | 9/1932 | Heard | 285/148.6 |
| 3,436,438 A | * | 4/1969 | Hokari et al. | 203/9 |
| 4,457,517 A | * | 7/1984 | Dunegan | 277/608 |
| 6,409,886 B1 | * | 6/2002 | Matsumoto et al. | 203/8 |
| 6,585,862 B1 | * | 7/2003 | Nishimura et al. | 203/8 |
| 7,268,254 B2 | * | 9/2007 | Olbert et al. | 562/598 |
| 7,393,992 B2 | * | 7/2008 | Hill et al. | 585/809 |
| 2010/0162816 A1 | * | 7/2010 | Bauchet et al. | 73/587 |

* cited by examiner

Primary Examiner — Duane Smith
Assistant Examiner — Ives Wu
(74) Attorney, Agent, or Firm — Oblon, Spivak, McClelland, Maier & Neustadt, L.L.P.

(57) ABSTRACT

A process is proposed for distillatively obtaining pure 1,3-butadiene from crude 1,3-butadiene in a plant comprising one or more distillation columns, comprising supply of a feed stream of crude 1,3-butadiene to the one distillation column or the first of the plurality of distillation columns, the one distillation column or the plurality of distillation columns having a flange with an internal diameter of ≧80 mm, comprising two mutually opposite plane-parallel surfaces (1) with an intermediate seal (2) which seals the interior of the one distillation column or of the first of the plurality of distillation columns from an intermediate space (3) on the atmosphere side between the two mutually opposite plane-parallel surfaces (1), and the intermediate space (3) on the atmosphere side between the two mutually opposite plane-parallel surfaces (1) being closed off from the atmosphere to form a chamber, wherein the chamber is purged continuously during the operation of the plant with a low-oxygen gas or a low-oxygen liquid comprising 1% by weight of molecular oxygen or less, based on the total weight of the low-oxygen gas or of the low-oxygen liquid.

20 Claims, 1 Drawing Sheet

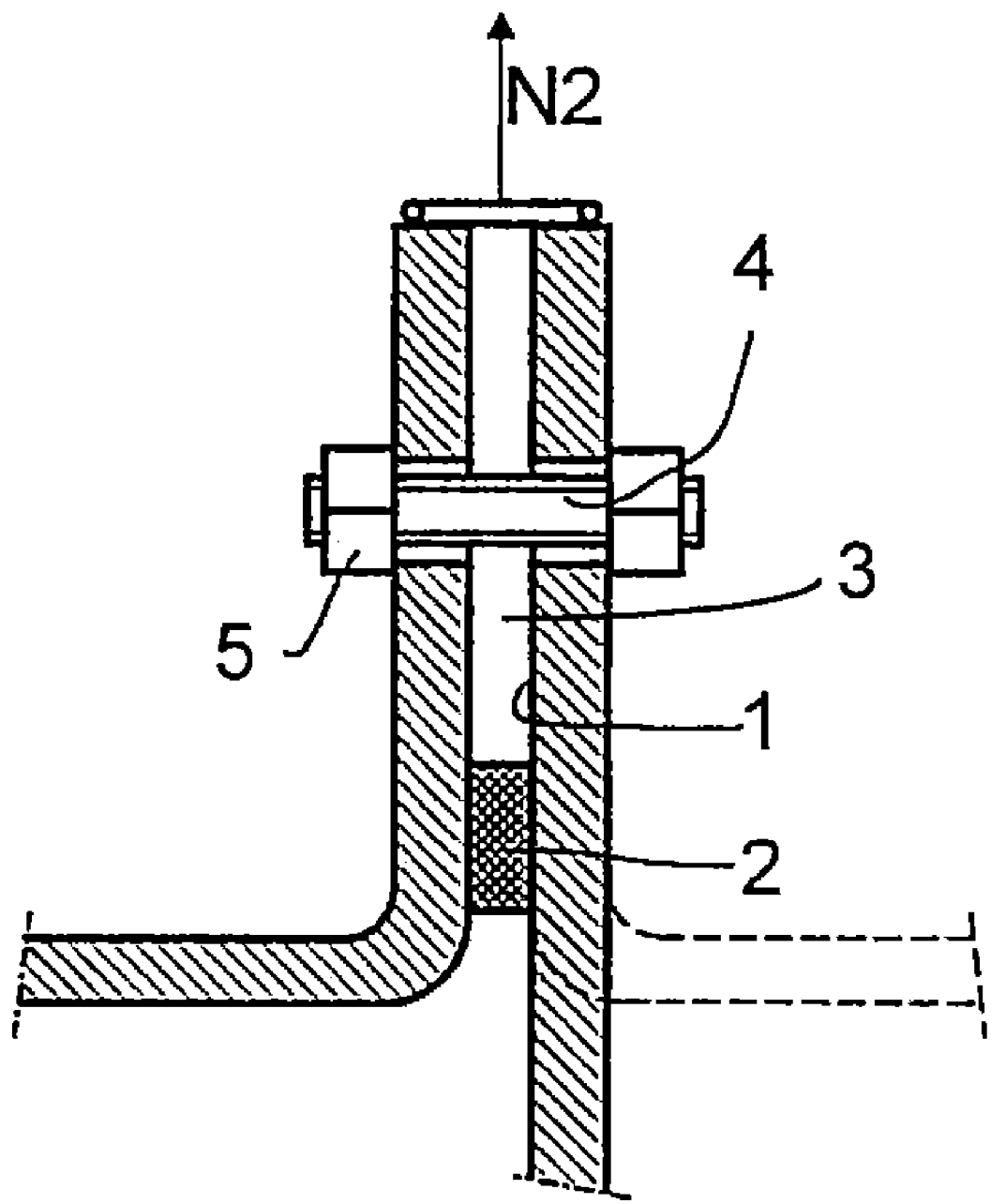

PROCESS FOR DISTILLATIVELY OBTAINING PURE 1,3-BUTADIENE FROM CRUDE 1,3-BUTADIENE

The invention relates to a process for distillatively obtaining pure 1,3-butadiene from crude 1,3-butadiene.

Crude 1,3-butadiene is obtained by extractive distillation from $C_4$ cuts.

The composition of the crude 1,3-butadiene depends on the composition of the $C_4$ cut which has been supplied to the extractive distillation, and generally comprises about half of the 1,2-butadiene from the $C_4$ cut, not more than 10% of the cis-2-butene and at least 98% of the 1,3-butadiene from the $C_4$ cut.

$C_4$ cuts generally have compositions, in % by weight, within the ranges below:

| | |
|---|---|
| 1,3-butadiene | 10 to 80 |
| butenes | 10 to 60 |
| butanes | 5 to 40 |
| other $C_4$ hydrocarbons and other hydrocarbons, especially $C_3$ and $C_5$ hydrocarbons | 0.1 to 5 |
| | 0 to not more than 5. |

Crude 1,3-butadiene is thus a stream with a 1,3-butadiene content of generally from about 95 to 99% by weight.

Pure 1,3-butadiene is obtained therefrom by distillation.

In the present context, the term "pure 1,3-butadiene" refers to a stream with a 1,3-butadiene content of at least 99.5% by weight, preferably of at least 99.7% by weight, the remainder being impurities, especially 1,2-butadiene and cis-2-butene.

Irrespective of the specific configuration of the plant for distillatively obtaining pure 1,3-butadiene from crude 1,3-butadiene, there exists in all plants the risk in which 1,3-butadiene-containing streams are distilled, at 1,3-butadiene concentrations of >80% by weight, that so-called popcorn polymer will form. Popcorn polymer is a specific form of butadiene polymer whose formation is initiated even by small traces of oxygen, for example in molecular form as peroxide or in the form of rust. Owing to its extremely rigid, three-dimensional structure and its growth behavior, popcorn polymer can exert extreme forces; this has previously led to many condensers and conduits breaking open. Popcorn polymer is thus extremely hazardous for the operation of plants for distillative workup of 1,3-butadiene.

In order to initialize the formation of popcorn, oxygen is required. The most important source thereof is leaks, especially at relatively large flanges, i.e. at flanges with an internal diameter of 80 mm or greater, or with an internal diameter of $\geq 200$ mm or even of $\geq 400$ mm, as are found, for example, in manholes or heat exchangers. Owing to the extremely high concentration difference between the surrounding atmosphere and the interior of the plant, within which the oxygen concentration is ideally 0, oxygen diffuses into the plant in spite of elevated pressure.

In order to prevent oxygen from diffusing in, the relatively large flanges in plants for distillatively obtaining pure 1,3-butadiene are tested regularly for leaks, and oxygen monitoring is carried out in the inert discharge from the condensers of the plants. In general, inhibitors are also used, which are intended to suppress popcorn formation. Nevertheless, it has been possible to date to limit popcorn formation only to an unsatisfactory degree.

It was therefore an object of the invention to provide a process for distillatively obtaining pure 1,3-butadiene, in which the formation of popcorn polymer can be substantially or completely prevented.

The object is achieved by a process for distillatively obtaining pure 1,3-butadiene from crude 1,3-butadiene in a plant comprising one or more distillation columns, comprising supply of a feed stream of crude 1,3-butadiene to the one distillation column or the first of the plurality of distillation columns, the one distillation column or the plurality of distillation columns having a flange with an internal diameter of $\geq 80$ mm, comprising two mutually opposite plane-parallel surfaces with an intermediate seal which seals the interior of the one distillation column or of the first of the plurality of distillation columns from an intermediate space on the atmosphere side between the two mutually opposite plane-parallel surfaces, and the intermediate space on the atmosphere side between the two mutually opposite plane-parallel surfaces being closed off from the atmosphere to form a chamber, wherein the chamber is purged continuously during the operation of the plant with a low-oxygen gas or a low-oxygen liquid comprising 1% by weight of molecular oxygen or less, based on the total weight of the low-oxygen gas or of the low-oxygen liquid.

The low-oxygen gas or the low-oxygen liquid has a proportion by weight of preferably $\leq 500$ ppm of molecular oxygen, more preferably of $\leq 100$ ppm of molecular oxygen, based in each case on the total weight of the low-oxygen gas or of the low-oxygen liquid.

The low-oxygen gas used is preferably nitrogen.

The inventors have recognized that conventional means of testing the flange for leaks are insufficient for the prevention of popcorn formation, since popcorn formation occurs even when the flange has been demonstrated to be leak free with conventional means. However, this popcorn formation can be reduced or prevented by purging the flanges, as proposed by the inventors, continuously with nitrogen during the operation of the plant.

The process is preferably performed in the presence of a substance which inhibits popcorn formation, especially in the presence of tert-butylpyrocatechol.

The closure of the intermediate space on the atmosphere side between the two mutually opposite plane-parallel surfaces to form a chamber can advantageously be achieved by winding a belt around it.

The belt may especially be a metal belt, especially a stainless steel belt, or a plastics belt, especially a PVC belt.

The belt can preferably be placed into a sealant material.

The flanges are generally secured with screws and nuts, which are preferably placed into a sealant material.

The continuous purging of the chambers is preferably carried out with a volume flow of from 5 to 15 l/h of low-oxygen gas or low-oxygen liquid per meter of nominal width of the orifice to which the particular flange is attached.

It has additionally been noted that the slightest unevenness of the flange is one factor responsible for the popcorn formation which still remains in spite of nitrogen purging.

In a preferred configuration of the process, the flanges are therefore designed with a narrow measurement tolerance, of $\leq 0.3$ mm.

More particularly, the flanges, in order to reliably prevent popcorn formation, can be completely welded shut. At such flanges, popcorn formation has been reduced to zero.

It has been found that a further critical site for the formation of popcorn is the feed tray at which the feed stream is introduced. In the case of a temperature difference of 20° C. or more between the feed stream and the column interior, 1,3-butadiene can be condensed on the underside of the feed tray, hence resulting, because this condensate is not inhibited, in popcorn formation. It has been found that this source of risk can reliably be eliminated by heating the feed stream to a temperature which differs from the temperature in the interior of the column to which the feed stream is supplied by not more than 10° C., preferably by not more than 5° C.

By reducing or preventing the formation of popcorn, the process according to the invention ensured increased reliability in the operation of the plants and prolonged run times.

The invention is illustrated in detail with reference to a drawing and to embodiments.

The sole FIGURE is a schematic diagram of a section through a flange on a distillation column, the flange closing off the interior of the column from the atmosphere.

The flange has two mutually opposite plane-parallel surfaces 1 with an intermediate seal 2 which seals the interior of the column from the atmosphere. In order to prevent oxygen from diffusing from the atmosphere through the seal into the interior of the column, in accordance with the invention, the intermediate space 3 on the atmosphere side between the plane-parallel surfaces 1 of the flange are sealed off from the atmosphere, for example by winding a metal belt around it to form a closed chamber which is purged continuously with a small nitrogen stream. The flange is secured by screws 4 and nuts 5.

EMBODIMENTS

In a distillation column for performing an industrial scale process for purifying distillation of crude 1,3-butadiene, with a column diameter of 1.70 m and a column height of 45 m, the column having been equipped with a total of 6 flanges, each with an internal diameter of 600 mm, the popcorn formation rate was examined without (for comparison) and with nitrogen purging of all flanges (inventive). The flanges were purged continuously with 4 l/h of nitrogen for each flange. The flanges were tested continuously for leaks.

From the bottom stream of the first column, which had the above dimensions and the above-specified 6 flanges, and which was used to remove low boilers via the top stream (so-called propyne column) the bottom stream was passed continuously through a filter and the popcorn deposits were studied in the filter: in the case of operation of the column without nitrogen purging (for comparison), approx. 50-100 g of popcorn polymer were discovered in the filter after two months.

In contrast, in the case of the inventive operation of the column, with continuous nitrogen purging of the flanges, only 60 g of popcorn polymer were discovered in the filter, through which the bottom stream was passed, after an operating time of 2 years.

In further operational tests, the influence of flange unevenness on the popcorn formation rate was studied:

After an operating time of 2 years, all flanges which, as specified above, had been purged continuously with in each case 4 l/h of nitrogen per flange were opened and examined for popcorn formation:

In the case of flanges with a tolerance of 0.3 mm, no popcorn was found.

The amount of popcorn found rose, in contrast, continuously with increasing tolerance, up to approx. 200 g, for a flange with a tolerance of 1.5 mm, after an operating time of 2 years.

The invention claimed is:

1. A process for distillatively obtaining pure 1,3-butadiene from crude 1,3-butadiene in a plant comprising one or more distillation columns, the process comprising supplying a feed stream of crude 1,3-butadiene to the one distillation column or a first of the plurality of distillation columns,
wherein
the one distillation column or the plurality of distillation columns have a flange with an internal diameter of at least 80 mm, the flange comprising two mutually opposite plane-parallel surfaces with an intermediate seal which seals an interior of the one distillation column or of the first of the plurality of distillation columns from an intermediate space on an atmosphere side between the two mutually opposite plane-parallel surfaces, and the intermediate space on the atmosphere side between the two mutually opposite plane-parallel surfaces is closed off from the atmosphere to form a chamber, wherein the chamber is purged continuously during the operation of the plant with nitrogen comprising 1% by weight of molecular oxygen or less, based on a total weight of the nitrogen.

2. The process according to claim 1, wherein the nitrogen comprises 500 ppm by weight of molecular oxygen or less, based on the total weight of the nitrogen.

3. The process according to claim 1, wherein the intermediate space on the atmosphere side between the two mutually opposite plane-parallel surfaces is closed to form a chamber by winding a belt around it.

4. The process according to claim 3, wherein the belt is a metal belt, or a plastic belt.

5. The process according to claim 4, wherein the belt is placed into a sealant material.

6. The process according to claim 1, wherein the flange is secured with screws and nuts which are placed into a sealant material.

7. The process according to claim 1, wherein the continuous purging of the chamber is performed with a volumetric flow rate of 3 to 15 l/h of the nitrogen per meter of nominal width of an orifice to which the flange is attached.

8. The process according to claim 1, wherein the flange has a measurement tolerance of at most 0.3 mm.

9. The process according to claim 1, wherein the feed stream of crude 1,3-butadiene, before being supplied to the one distillation column or to the first of the plurality of distillation columns, is heated to a first temperature, an interior of the column is at a second temperature, and the first and second temperatures differ by not more than 10° C.

10. A process for distillatively obtaining pure 1,3-butadiene from crude 1,3-butadiene in a plant comprising one or more distillation columns, the process comprising supplying a feed stream of crude 1,3-butadiene to the one distillation column or a first of the plurality of distillation columns,
wherein
the one distillation column or the plurality of distillation columns have a flange with an internal diameter of at least 80 mm, the flange comprising two mutually opposite plane-parallel surfaces with an intermediate seal which seals an interior of the one distillation column or of the first of the plurality of distillation columns from an intermediate space on an atmosphere side between the two mutually opposite plane-parallel surfaces, and the intermediate space on the atmosphere side between the two mutually opposite plane-parallel surfaces is closed off from the atmosphere to form a chamber, wherein the chamber is purged continuously during the operation of the plant with a low-oxygen gas or a low-oxygen liquid comprising 1% by weight of molecular oxygen or less, based on a total weight of the low-oxygen gas or of the low-oxygen liquid,
wherein the continuous purging of the chamber is performed with a volumetric flow rate of 3 to 15 l/h of the low-oxygen gas or the low-oxygen liquid per meter of nominal width of an orifice to which the flange is attached.

11. The process according to claim 10, wherein the low-oxygen gas or the low-oxygen liquid comprises 500 ppm by weight of molecular oxygen or less, based on the total weight of the low-oxygen gas or of the low-oxygen liquid.

12. The process according to claim 10, wherein the intermediate space on the atmosphere side between the two mutually opposite plane-parallel surfaces is closed to form a chamber by winding a belt around it.

13. The process according to claim 12, wherein the belt is a metal belt, or a plastic belt.

14. The process according to claim 13, wherein the belt is placed into a sealant material.

15. A process for distillatively obtaining pure 1,3-butadiene from crude 1,3-butadiene in a plant comprising one or more distillation columns, the process comprising supplying a feed stream of crude 1,3-butadiene to the one distillation column or a first of the plurality of distillation columns,
wherein
the one distillation column or the plurality of distillation columns have a flange with an internal diameter of at least 80 mm, the flange comprising two mutually opposite plane-parallel surfaces with an intermediate seal which seals an interior of the one distillation column or of the first of the plurality of distillation columns from an intermediate space on an atmosphere side between the two mutually opposite plane-parallel surfaces, and the intermediate space on the atmosphere side between the two mutually opposite plane-parallel surfaces is closed off from the atmosphere to form a chamber, wherein the chamber is purged continuously during the operation of the plant with a low-oxygen gas or a low-oxygen liquid comprising 1% by weight of molecular oxygen or less, based on a total weight of the low-oxygen gas or of the low-oxygen liquid,
wherein the feed stream of crude 1,3-butadiene, before being supplied to the one distillation column or to the first of the plurality of distillation columns, is heated to a first temperature, an interior of the column is at a second temperature, and the first and second temperatures differ by not more than 10° C.

16. The process according to claim 15, wherein the low-oxygen gas or the low-oxygen liquid comprises 500 ppm by weight of molecular oxygen or less, based on the total weight of the low-oxygen gas or of the low-oxygen liquid.

17. The process according to claim 15, wherein the intermediate space on the atmosphere side between the two mutually opposite plane-parallel surfaces is closed to form a chamber by winding a belt around it.

18. The process according to claim 17, wherein the belt is a metal belt, or a plastic belt.

19. The process according to claim 18, wherein the belt is placed into a sealant material.

20. The process according to claim 15, wherein the continuous purging of the chamber is performed with a volumetric flow rate of 3 to 15 l/h of the low-oxygen gas or the low-oxygen liquid per meter of nominal width of an orifice to which the flange is attached.

* * * * *